United States Patent
Eriksson

(10) Patent No.: US 7,912,546 B2
(45) Date of Patent: Mar. 22, 2011

(54) METHOD AND APPARATUS FOR DETERMINING A REPLACEMENT TIME OF AN ELECTRIC BATTERY

(75) Inventor: Tom Eriksson, Sandviken (SE)

(73) Assignee: St. Jude Medical AB, Jarfalla (SE)

( * ) Notice: Subject to any disclaimer, the term of this patent is extended or adjusted under 35 U.S.C. 154(b) by 534 days.

(21) Appl. No.: 11/910,761

(22) PCT Filed: May 9, 2005

(86) PCT No.: PCT/SE2005/000666
§ 371 (c)(1),
(2), (4) Date: May 30, 2008

(87) PCT Pub. No.: WO2006/107247
PCT Pub. Date: Oct. 12, 2006

(65) Prior Publication Data
US 2008/0262560 A1 Oct. 23, 2008

(30) Foreign Application Priority Data
Apr. 7, 2005 (WO) .................. PCT/SE2005/000508

(51) Int. Cl.
*A61N 1/37* (2006.01)

(52) U.S. Cl. ......................................................... 607/29
(58) Field of Classification Search ...................... 607/29
See application file for complete search history.

(56) References Cited

U.S. PATENT DOCUMENTS

| 5,370,668 | A | 12/1994 | Shelton et al. |
| 5,889,388 | A | 3/1999 | Cameron et al. |
| 5,925,068 | A | 7/1999 | Kroll |
| 6,748,273 | B1 | 6/2004 | Obel et al. |
| 2003/0149455 | A1 | 8/2003 | Obel et al. |
| 2004/0039424 | A1 | 2/2004 | Merritt et al. |
| 2005/0007073 | A1 | 1/2005 | James et al. |

*Primary Examiner* — Michael Kahelin
(74) *Attorney, Agent, or Firm* — Schiff Hardin LLP

(57) ABSTRACT

In a method and apparatus for determining the replacement time of an electric battery in an implantable medical device, the battery being a hybrid battery with a combination of at least two electrode materials, one of which having better properties for high current pulsing and the other of which being a high energy density material, an electrical pulse of a predetermined duration and predetermined amplitude is drawn from the battery. The pulse amplitude significantly exceeds a base current drawn from the battery. The difference between voltages measured across the battery terminals before the pulse is emitted and at an end of the pulse is determined. The battery replacement time is determined from the voltage difference according to a predetermined criterion.

13 Claims, 2 Drawing Sheets

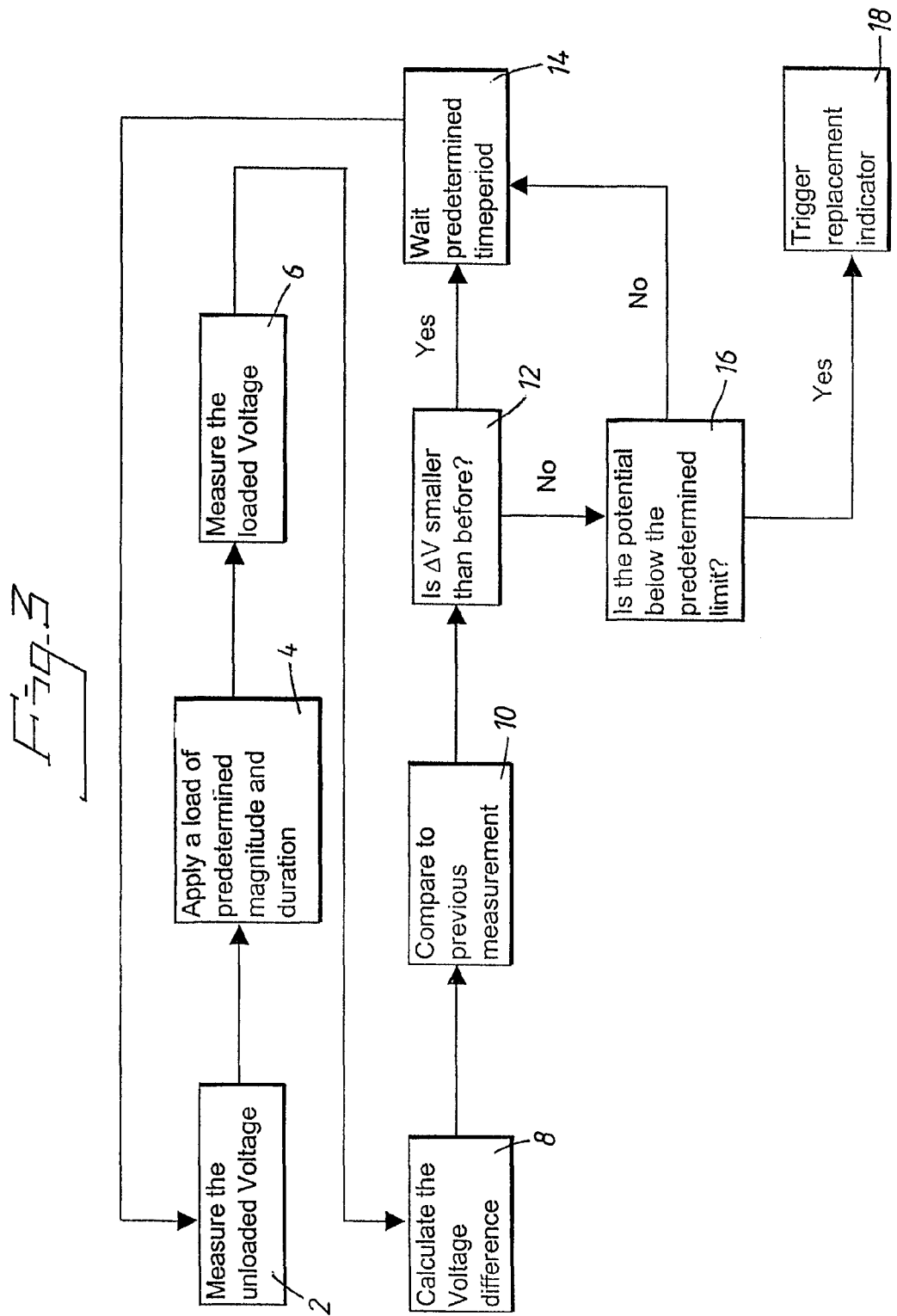

METHOD AND APPARATUS FOR DETERMINING A REPLACEMENT TIME OF AN ELECTRIC BATTERY

BACKGROUND OF THE INVENTION

1. Field of the Invention

The present invention relates to a method of determining a replacement time of an electric battery of an implantable medical device, IMD, the battery being a hybrid battery with a combination of at least two electrode materials, one electrode material having better properties for high current pulsing and the other electrode material being a high energy density material. The invention also relates to a corresponding apparatus.

2. Description of the Prior Art

The control of status of the battery of implantable electrical medical devices is very important for reliably determining a suitable battery replacement time. Different techniques have been used for this purpose.

Controlling the battery status by merely making a voltage reading has appeared not to be reliable.

Impedance measurements on the battery, possibly combined with charge depletion measurements, are well known, see e.g. U.S. Pat. No. 6,748,273 and United States Application Publication No. 2003/0149455. In U.S. Pat. No. 5,925,068 the use of combined measurements of battery terminal voltage and charge time of a capacitor for determining a recommended battery replacement time is described.

In United States Publication No. 2005/0007073 determination of an indicator of remaining energy in a battery of an IMD is described. The battery is of a type like a manganese dioxide (MnO2) or silver vanadium oxide (SVO) battery having a flat quiescent battery voltage during a beginning of the battery life time. A constant load current is then drawn from the battery during a time period of 3 to 30 seconds and the battery terminal voltage is measured during this period. The rate of change, slope or polarization angle of this voltage is determined and compared with stored data from similar batteries to determine remaining energy of the battery.

A way of checking the battery status which is adapted to the specific type of battery and its chemical characteristics would result in an improved possibility of checking battery status.

A direct measurement of terminal voltage or of the battery internal resistance can also be used for determining the status of hybrid batteries, like lithium silver vanadium oxide, Li/SVO, batteries and lithium iodine batteries. A constant reference value is then set and measured values are compared with this reference value.

SUMMARY OF THE INVENTION

An object of the present invention is to provide a simple and reliable determination of suitable replacement time of electric hybrid batteries of IMDs based on the specific characteristics of the batteries in question.

The above object is achieved in accordance with the present invention by a method and an apparatus for determining the replacement time of an electric battery of an implantable medical device, the battery being a hybrid battery with a combination of at least two electrode materials, with one of the electrode materials having better properties for high current pulsing and the other of the electrode materials being a high energy density material. In accordance with the invention, an electrical pulse of a predetermined duration and a predetermine amplitude is drawn from the battery, the pulse amplitude thereof significantly exceeding a base current that is drawn from the battery, and the difference between voltages measured between the battery terminals before the pulse is emitted and at an end of the pulse is determined. A battery placement time is determined from this voltage difference, according to a predetermined criterion.

The invention is thus based on the insight that hybrid batteries of IMDs having a combination of two or more electrode materials have specific characteristics that can be used for providing battery specific battery replacement indication triggers. By using an electrode material with better properties for high current pulsing, viz. a high power density material, combined with a high energy density electrode material a convergence in the drop of the battery terminal voltage, when current pulses are drawn from the battery, is observed, provided that the high power density material has a lower voltage plateau than the high energy density material. This phenomenon is used in the present invention for determining a battery replacement time.

For this kind of batteries the difference between the voltage measured between the battery terminals before the pulse is emitted and at the end of the pulse has a minimum value for a state of charge, SOC, which can be tuned by controlling the amount of each cathode material component used. In the present applications a SOC of typically about 25% could be a suitable level for triggering a battery replacement indication. The batteries in question are thus manufactured by using suitable amounts of cathode material components. According to embodiments of the invention the voltage difference is compared with previously determined voltage differences to determine when the voltage difference has reached a minimum value to then trigger a battery replacement indicator, or, alternatively, the derivative of the $d(\Delta V)/d(SOC)$ is determined and a battery replacement indicator is triggered when the derivative changes sign from negative to positive, where $\Delta V$ denotes the voltage difference and SOC state of charge of the battery.

The occurrence of this minimum in the difference between the battery terminal voltages measured before the measuring pulse is emitted and at the end of the pulse can also be related to the charge drawn from the battery or to the time, when the battery is in normal use with a base current drawn from the battery. Thus according to other advantageous embodiments of the invention the derivative $d(\Delta V)/dQ$ or $d(\Delta V)/dt$ is determined and a battery replacement indicator is triggered when the derivative changes sign from negative to positive, where Q and t denote the charge drawn from the battery and the time of normal use of the battery, respectively. These embodiments are advantageous, since Q and t are quantities which can be directly measured.

According to another embodiment of the invention the measured battery terminal voltage is compared with a predetermined limit value, and a battery replacement indicator is triggered only if the battery voltage has dropped below the predetermined limit value. By this check of the level of the voltage the risk of triggering false battery replacement indicators early in the battery lifetime due to accidental fluctuations in the voltage measurements is reduced.

To avoid problems related to a quick drop in the battery terminal voltage at the beginning of the battery life time when the battery is almost fully charged, pulses drawn from the battery for determining the battery replacement time, are drawn for the first time not until the voltage has dropped below a predetermined voltage limit value according to yet another advantageous embodiment of the invention.

According to still other embodiments of the invention the pulse amplitude is selected large enough, preferably in the range of 1-100 mA, for getting a significant, detectable value of said voltage difference, preferably exceeding 30 mV, and the duration of the pulse is selected short enough, preferably of the order of msec., for avoiding significant charge drain from the battery. By using a short pulse disturbance of the IMD functionality is avoided as well.

BRIEF DESCRIPTION OF THE DRAWINGS

FIG. 3 is a flowchart in the form of a block diagram illustrating an embodiment of the method according to the invention.

DESCRIPTION OF THE PREFERRED EMBODIMENTS

Figure 1:
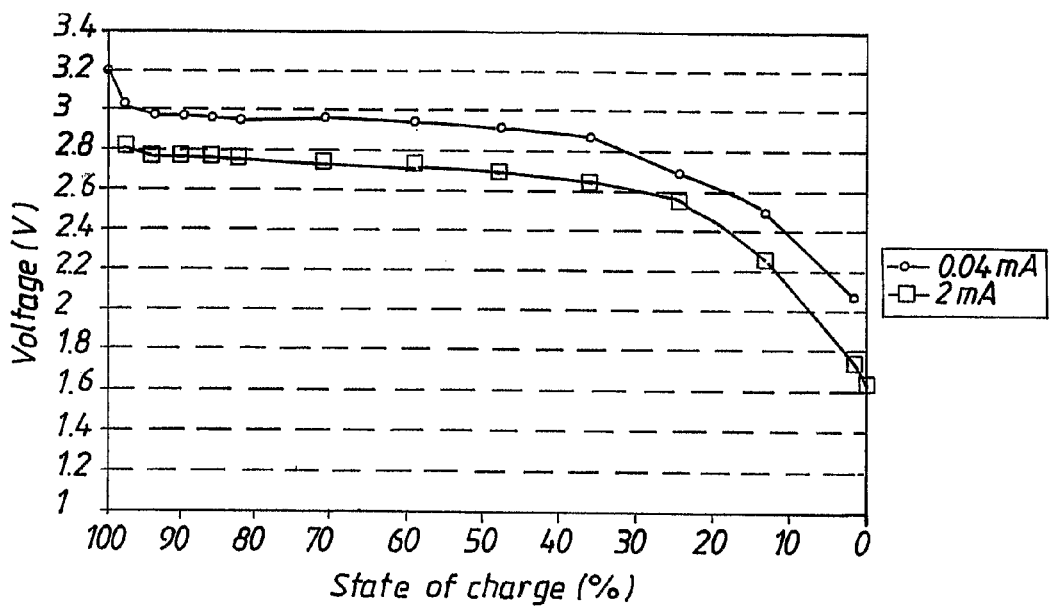
FIG. 1 is a graph showing curves for a base current drawn from the battery, as used in accordance with the present invention.
Figure 2:
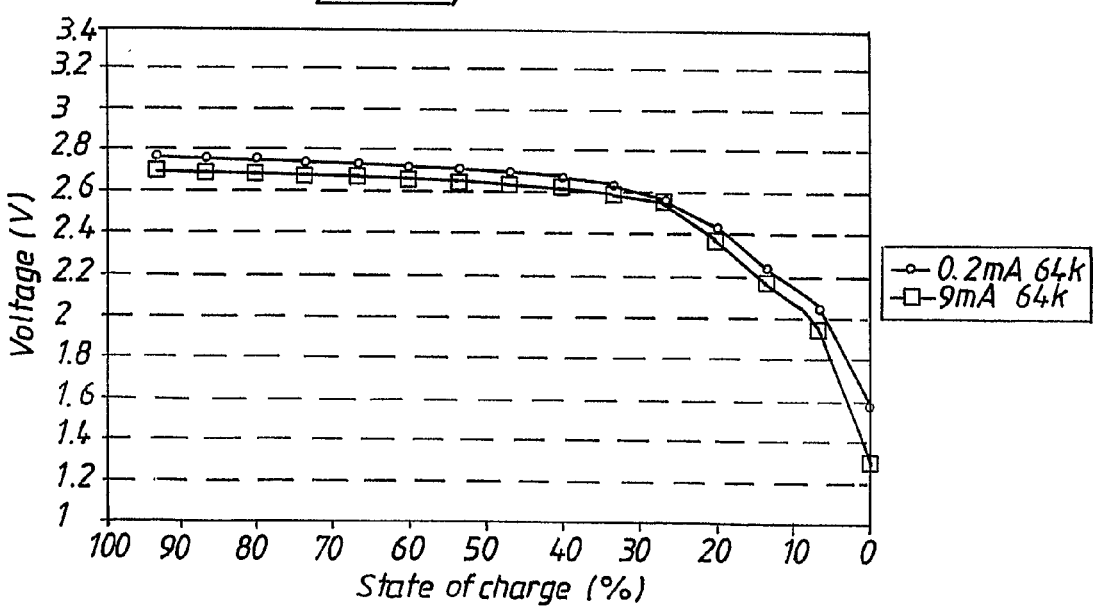
FIG. 2 is a graph showing curves for the base current drawn from the battery as in FIG. 1, but with a higher loading of the battery.

Hybrid batteries with two or more electrode materials used in combination have specific characteristics as mentioned above. These characteristic properties can be utilized for providing tailor-made battery replacement indication triggers. Batteries having one high power density electrode material with better properties for high current pulsing, i.e. a "quick" material, in combination with a high energy density material, i.e. a more "slow" material capable of delivering current for longer time, the difference between the battery terminal voltage measured before a current pulse is drawn from the battery and at the end of this pulse presents a minimum value for a certain state of charge value, SOC, of the battery, provided that the high power density material has a lower voltage plateau than the high energy density material, as explained above. This is illustrated in FIGS. 1 and 2. These figures show the battery terminal voltage as a function of the state of charge for a hybrid battery marketed by the company Wilson Greatbatch as hybrid Quasar battery M2370. FIG. 1 shows curves for a base current drawn from the battery of 0.04 mA and pulses with an amplitude of 2 mA. FIG. 2 illustrates a situation of higher loading of the battery, viz. a base current of 0.2 mA and a pulse current of 9 mA. After the minimum the voltage difference is again increasing for both cases shown in FIGS. 1 and 2.

In case of a pacemaker a baseline current, very likely not exceeding 10 µA, will be drawn. In addition thereto current will be drawn for stimulation pulses to the patient's heart. The sum of these two currents will in practice be of the order of 10-20 µA. However, also in this case the above-mentioned voltage difference presents a minimum value for the specified state of charge around 25%, as in the examples shown in FIGS. 1 and 2. As discussed above the SOC value for this voltage difference minimum is depending on the proportions of the different active cathode material components used.

The above-mentioned minimum in the voltage difference probably stems from the fact that the high energy density material has a higher electrochemical potential, E, and is first used up and the high power material, which has a lower E, then starts to be used to a larger extent. The material with the highest E will thus be used up first.

Thus, in the present invention a pulse of predetermined time length and a predetermined amplitude is drawn from the battery with predetermined time intervals. A typically one millisecond long pulse is emitted, e.g. once a day. The battery terminal voltage is recorded before the pulse is emitted and at the end of the pulse, and the difference between these measured voltages is calculated.

The pulse current must be large enough for obtaining a significant and clearly detectable voltage difference, preferably >30 mV. The pulse duration must be short enough to avoid current drain from the battery and disturbance of the IMD functionality. The pulse duration is preferably in the msec range.

The above discussed minimum in the determined difference between the battery terminal voltage, measured before the pulse is drawn from the battery and at the end of the pulse, which appears for a battery state of charge specified to approximately 25% in the present embodiment, is then used for triggering a battery replacement indicator, viz, the battery replacement time is determined from the occurrence of this minimum.

FIG. 3 is a flow chart illustrating an embodiment of the invention for the determination of a replacement time for a hybrid battery of the above described type for an implantable medical device.

The unloaded battery terminal voltage, viz. the terminal voltage when only the base current is drawn from the battery, is first measured, at step 2 in FIG. 3. A load is then applied on the battery in the form of a pulse of predetermined magnitude and duration, at step 4, and the battery terminal voltage is measured at the end of the pulse, at step 6.

The difference between the voltage measured in step 2 and in step 6 is calculated, at step 8. The voltage difference calculated in step 8 is then compared with corresponding voltage differences obtained from previous measurements, at step 10 in FIG. 3. If the latest voltage difference ΔV is smaller than previous voltage differences, step 12, the measurement is repeated after a predetermined time period, e.g. after 24 hours as mentioned above, step 14 in FIG. 3.

If the calculated voltage difference ΔV is not smaller than the preceding voltage difference, step 12 in FIG. 3, the minimum value is reached or has been passed. It is then checked that the measured voltage difference is below a predetermined limit value, at step 16. If so, a battery replacement indicator is triggered, at step 18 in FIG. 3.

If the measured voltage difference is not below the predetermined limit value at step 16 the measurements are repeated after the predetermined time period, step 14. By this check of the level of the voltage the risk of triggering false battery replacement indicators earlier in the battery lifetime due to accidental fluctuations in the voltage measurements is reduced. As can be seen from FIGS. 1 and 2 the battery voltage has a substantially flat level for a major part of the battery state of charge region, and when the voltage difference reaches its minimum for a battery state of charge of about 25% the battery voltage has dropped somewhat from this flat level, which makes it possible to set a suitable voltage limit value for the mentioned check of the voltage level. In the examples illustrated in FIGS. 1 and 2 this limit value can be selected in the range of 2.6 to 2.8 V.

As an alternative to the embodiment described above pulses can be drawn from the battery for the purpose of determining the battery replacement time not until the battery voltage has dropped below the predetermined limit value.

The invention can also include a differentiator for forming the derivative $d(\Delta V)/d(SOC)$, and when the derivative changes sign from a negative to a positive value a battery replacement indicator is triggered (provided that battery voltage level is below the limit value). ΔV denotes the voltage difference and SOC state of charge of the battery.

The battery terminal voltage V as a function of the charge Q drawn from the battery or as a function of time t, when the battery is in use with a base current drawn from the battery, shows a behavior which is qualitatively similar to the curves in FIGS. 1 and 2. Thus the invention can also include a differentiator for forming the derivative $d(\Delta V)/dQ$ or $d(\Delta V)/dt$, instead of the derivative $d(\Delta V)/d(SOC)$, and when these derivatives change sign from a negative to a positive value a battery replacement indicator is triggered (provided that battery voltage level is below the limit value). This is advantageous since Q and t are directly measurable quantities.

The apparatus according to the invention, e.g. a heart stimulator, has suitable switching circuitry for connecting a load to the battery for drawing a measurement pulse of predetermined amplitude ad duration from the battery, as discussed above. The apparatus also includes a measuring circuit for measuring the battery terminal voltage immediately before the load is connected, viz. immediately before the beginning of the measurement pulse, and immediately before the disconnection of the load, viz. immediately before the end of the measurement pulse. A circuit designed as a current generator can then preferably be used for drawing a measurement pulse from the battery of substantially constant amplitude.

The apparatus according to the invention also includes a voltage difference former, a replacement time determining unit, e.g. in the form of a comparator, and, where appropriate, a differentiator.

These electric components and circuits are well-known to those skilled in the art and need not be described in greater detail.

A large number of different electrode materials are possible for the hybrid batteries, cf. U.S. Pat. No. 6,551,747. Thus a first electrode material can be selected from the group consisting of $CF_x$, $Ag_2O$, $Ag_2O_2$, $CuF$, $Ag_2CrO_4$, $MnO_2$, SVO and mixtures thereof. A second electrode material from the group consisting of SVO, CSVO, $V_2O_5$, $MnO_2$, $LiCoO_2$, $LiNiO_2$, $LiMnO_2$, $CuO_2$, TiS, $Cu_2S$, FeS, $FeS_2$, $V_6O_{13}$, copper oxide, copper vanadium oxide, and mixtures thereof.

Although modifications and changes may be suggested by those skilled in the art, it is the intention of the inventor to embody within the patent warranted heron all changes and modifications as reasonably and properly come within the scope of his contribution to the art.

I claim as my invention:

1. An implantable medical device comprising:
   a hybrid battery comprising a combination of at least two electrode materials, a first of said electrode materials having better properties for high current pulsing than a second of said materials, and said second of said materials being a high energy density material;
   circuitry powered by said battery configured to interact with a living subject to administer electrical therapy to the subject;
   an apparatus that determines a replacement time of said battery by determining a base current that is drawn from the battery, and by drawing an electrical pulse of a predetermined duration and a predetermined amplitude from the battery, said pulse amplitude significantly exceeding said base current, automatically determining a difference between a first voltage measured between the battery terminals before emitting said pulse and a second voltage measured between the battery terminals at an end of the pulse, and automatically determining a replacement time for said battery from said voltage difference according to a predetermined criterion and triggering a battery replacement indicator when said time has been reached.

2. An implantable medical device as claimed in claim 1 wherein said apparatus automatically determines said replacement time by automatically comparing said voltage difference, as a current voltage difference, with a plurality of previously determined voltage differences from the battery and, from a result of the comparison, by automatically determining when the current voltage difference reaches a minimum value, and thereupon automatically triggers said battery replacement indicator.

3. An implantable medical device as claimed in claim 1 wherein said apparatus automatically determines said battery replacement time by determining a state of charge (SOC) of the battery, and by automatically calculating a derivative $d(\Delta V)/d(SOC)$, wherein $\Delta V$ is said voltage difference, and automatically triggers said battery replacement indicator when the derivative changes sign from negative to positive.

4. An implantable medical device as claimed in claim 1 wherein said apparatus automatically determines said battery replacement time by identifying a charge Q drawn from the battery and automatically calculating a derivative $d(\Delta V)/dQ$, wherein $\Delta V$ is said voltage difference, and automatically triggers said battery replacement indicator when the derivative changes sign from negative to positive.

5. An implantable medical device as claimed in claim 1 wherein said apparatus automatically determines said battery replacement time by automatically calculating a derivative $d(\Delta V)/dt$, wherein $\Delta V$ is said voltage difference and t is time, and automatically triggers said battery replacement indicator when the derivative changes sign from negative to positive.

6. An implantable medical device as claimed in claim 1 wherein said apparatus automatically determines said battery replacement time by automatically comparing said voltage difference with a predetermined limit value, and automatically triggers said battery replacement indicator if said voltage difference falls below said predetermined limit value.

7. An implantable medical device as claimed in claim 1 wherein said apparatus compares a base voltage drawn from the battery at said base current, with a predetermined limit value, and triggers a battery replacement indicator only if said base voltage is below said predetermined limit value.

8. An implantable medical device claimed in claim 7 wherein said apparatus draws said pulse from the battery for a first time only after said base voltage has fallen below said predetermined limit value.

9. An implantable medical device as claimed in claim 1 wherein said apparatus causes said pulse to be emitted with said pulse amplitude being selected to cause a value of said voltage difference to exceed 30 mV.

10. An implantable medical device as claimed in claim 1 wherein said base current is in a range between 10 and 100 $\mu A$, and wherein said apparatus causes said pulse to be emitted with said amplitude in a range between 1 and 100 mA.

11. An implantable medical device as claimed in claim 1 wherein said apparatus causes said pulse to be emitted with a pulse duration in a range of multiple milliseconds.

12. An implantable medical device as claimed in claim 1 wherein said apparatus causes said pulse to be drawn from said battery, and automatically determines said voltage difference, once a day.

13. An implantable medical device as claimed in claim 1 wherein said hybrid battery comprises an electrode material, as first material, selected from the group consisting of $CF_x$, $Ag_2O$, $Ag_2O_2$, $CuF$, $Ag_2C_rO_4$, $MnO_2$, SVO, and mixtures thereof, and an electrode material, as said second material, selected from the group consisting of SVO, CSVO, $V_2O_5$, $MnO_2$, $LiCoO_2$, $LiNiO_2$, $LiMnO_2$, $CuO_2$, TiS, $Cu_2S$, FeS, $FeS_2$, $V_6O_{13}$, copper oxide, copper vanadium oxide, and mixtures thereof.

* * * * *